United States Patent [19]
Shibuya et al.

[11] Patent Number: 4,783,429
[45] Date of Patent: Nov. 8, 1988

[54] NO ALKALI CONTAINING BIOCOMPATIBLE GLASS CERAMIC WITH APATITE, WOLLASTONITE AND DIOPSIDE CRYSTALS MIXED

[75] Inventors: Takehiro Shibuya, Shiga; Yoshinori Morita; Akira Matsui, both of Kyoto, all of Japan

[73] Assignee: Nippon Electric Glass Company, Limited, Shiga, Japan

[21] Appl. No.: 33,995

[22] Filed: Apr. 2, 1987

[51] Int. Cl.$^4$ .................. C03C 10/02; C03C 10/04; C03C 10/16

[52] U.S. Cl. ............................ 501/5; 501/3; 501/10; 501/57; 501/58; 501/59; 501/63

[58] Field of Search .................. 501/5, 10, 3, 57, 58, 501/59, 63

[56] References Cited

U.S. PATENT DOCUMENTS 4,560,666 12/1985 Yoshida et al. .................. 501/5
4,643,982 2/1987 Kasuga et al. .................. 501/5
4,652,534 3/1987 Kasuga .................. 501/5

FOREIGN PATENT DOCUMENTS 57-191252 11/1982 Japan .
61-158841 7/1986 Japan .

Primary Examiner—Mark L. Bell
Attorney, Agent, or Firm—Hopgood, Calimafde Kalil, Blaustein & Judlowe

[57] ABSTRACT

A biocompatible glass ceramic comprises, by weight, 7–16% MgO, 20–45% CaO, 41–50% $SiO_2$, 8–30% $P_2O_5$, 0–5% $B_2O_3$, 0–5% $F_2$, and 0–10% $Al_2O_3$, and has a crystal structure where a number of fine crystals of apatite, wollastonite, and diopside are densely dispersed and interlace with one another in a glass phase. The glass ceramic is non-porous and has an increased mechanical strength of 2,000 Kg f/cm$^2$ without degradation of the chemical bonding with the bone of the living body. The glass ceramic contains no alkali and is chemically stable in the living body. The glass ceramic is useful for replacement materials of tooth roots and crowns as well as bones.

3 Claims, No Drawings

NO ALKALI CONTAINING BIOCOMPATIBLE GLASS CERAMIC WITH APATITE, WOLLASTONITE AND DIOPSIDE CRYSTALS MIXED

BACKGROUND OF THE INVENTION (1) Field of the Invention

The present invention relates to crystallized glass or glass ceramics, and, in particular, to biocompatible glass ceramics which are useful for artificial dental roots, artificial tooth crowns and others.

(2) Description of the Prior Art

It is needless to say that the biocompatible materials useful, for example, for tooth replacement materials, are required not to be harmful for living bodies such as human bodies and animal bodies. Among the other various requirements for those biocompatible materials, a high mechanical strength and an excellent biological affinity are also important.

Although alumina and sintered apatite are well known as typical and conventional biocompatible materials in the prior art, they have disadvantages. Alumina cannot be chemically bonded to bones and teeth of the living body, and therefore, any means is required to fixedly connect alumina to the living body. Sintered apatite has not a sufficient mechanical strength as replacements of the bones and the teeth.

In order to reduce the above-described disadvantages of alumina and sintered apatite, glass ceramics are used for biocompatible materials in the prior art. U.S. Pat. No. 3,922,155 by Broemer assigned to Ernst Leitz G.m.b.H. discloses a $Na_2O$—$K_2O$—$MgO$—$CaO$—$SiO_2$—$P_2O_3$ glass ceramic as a bone replacement material. The glass ceramic includes apatite crystals and has a good biological affinity. However, since the glass ceramic contains $Na_2O$ and $K_2O$, it is insufficient in the mechanical strength and has a low chemical resistance so that it is not maintained stable in the living body for a long time.

Also, $MgO$—$CaO$—$SiO_2$—$P_2O_5$ glass ceramics are disclosed for biocompatible materials in U.S. Pat. No. 4,560,666 by Yoshida et al assigned to Hoya Corporation and Japanese patent application laid open with No. 191252/'82. The glass ceramics contain $SiO_2$ which is restricted to 41 wt % or less in amount so as to increase apatite crystals dispersed therein, so that the glass ceramics are excellent in chemical bonding with bone. However, the glass ceramics are insufficient in the mechanical strength.

Japanese patent application laid open with No. 158841/'86 discloses another glass ceramic useful for a bone replacement material. The glass ceramic is a porous $CaO$—$P_2O_5$—$SiO_2$ glass ceramic having apatite crystals and diopside and/or wollastonite crystals. The glass ceramic is also insufficient in the mechanical strength.

SUMMARY OF THE INVENTION

It is an object of the present invention to provide a glass ceramic, as a biocompatible material, which has an improved excellent mechanical strength but with a good biological affinity similar to the known glass ceramics in the prior art.

According to the present invention, a high-strength and no alkali containing biocompatible glass ceramic is obtained which has a composition consisting essentially, by weight, of 7–16% $MgO$, 20–45% $CaO$, 41–50% $SiO_2$, 8–30% $P_2O_5$, 0–5% $B_2O_3$, 0–5% $F_2$, and 0–10% $Al_2O_3$. A total content of $MgO$, $CaO$, $SiO_2$ and $P_2O_5$ is 90% or more. The glass ceramic is substantially non-porous and has a mechanical strength of 2,000 Kg·f/cm$^2$ or more and a crystal structure where a number of fine crystals are densely dispersed in a glass phase.

A method for producing a no alkali containing biocompatible glass ceramic according to the present invention comprises steps of; preparing a glass powder having a particle size of 200 mesh or less and having a composition which consists essentially, by weight, of 7–16% $MgO$, 20–45% $CaO$, 41–50% $SiO_2$, 8–30% $P_2O_5$, 0–5% $B_2O_3$, 0–5% $F_2$, and 0–10% $Al_2O_3$; press-forming the glass powder into a compact body of a predetermined shape; heating the compact body to obtain a sintered body at a temperature within a glass powder sintering temperature range; and heat-treating the sintered body at a temperature within a crystallizing temperature range.

Preferably, the glass ceramic composition consists essentially, by weight, of 7.2–14% $MgO$, 25–38% $CaO$, 41.5–50% $SiO_2$, 8.2–25% $P_2O_5$, 0–4% $B_2O_3$, 0–3% $F_2$, and 0–6% $Al_2O_3$.

In the glass ceramic composition, a total content of $B_2O_3$ and $F_2$ is preferably 0.05–5%.

DETAILED DESCRIPTION OF THE INVENTION

In the glass ceramic according to the present invention, the fine and dense crystals comprises apatite crystals, wollastonite crystals, and diopside crystals which extend in respective particles of the powder inwardly from their outer surfaces and interlace in a complicated structure. The fine and dense crystals enhance the mechanical strength and the mechanical machinability of the glass ceramic, so that the glass ceramic can be easily machined into a desired shape without any crack and chipping of the ceramic.

The wollastonite and diopside crystals serve to increase the mechanical strength of the glass ceramic. The apatite crystals serve to make a good chemical bonding of the glass ceramic and the bone of the living body and enhance the biological affinity of the glass ceramic, as known in the prior art.

Description will be made below as to the reason why the amount of each component of the glass ceramic of the present invention is limited to the above-described range.

If MgO content is less than 7%, a resultant glass composition is devitrifiable so that the glass powder cannot hardly be prepared from a melt of the mixed raw materials. Further, an undesired small amount of the diopside crystals are only precipitated at the crystallizing temperature heat treatment. Therefore, the amount of MgO is 7% at minimum, or preferably 7.2% or more. The use of MgO more than 14% decreases an amount of apatite crystals formed in the glass phase. Therefore, MgO content is 16% at maximum, or preferably 14% or less.

When CaO amount is less than 25%, amounts of apatite and wollastonite crystals decrease. Therefore, CaO content must be preferably 25% or more, or 20% at minimum. If CaO content is more than 38%, a resultant glass composition is devitrifiable so that the glass powder cannot hardly be prepared from a melt of the mixed raw materials. Therefore, CaO content is preferably 38% or less and is 45% at maximum.

When $SiO_2$ content is less than 41%, amounts of diopside and wollastonite crystals are reduced. Therefore, $SiO_2$ content is 41% at minimum and is preferably 41.5% or more. The use of $SiO_2$ more than 50% increases viscosity of a melt of the resultant glass composition so that preparation of the glass powder is difficult. Further, a reduced amount of apatite crystals are only precipitated. Therefore, the amount of $SiO_2$ must be 50% or less.

Considering that those glass ceramics in the above-described U.S. Pat. No. 4,560,666 and Japanese patent application No. 191252/'82 contain $SiO_2$ which is restricted to 41 wt % or less to obtain an excellent chemical bonding with the bone, it is predicted that the glass ceramic of the present invention has a reduced apatite and cannot be sufficiently chemically bonded to the bone because the $SiO_2$ content is 41% or more. However, as will be noted from examples which are demonstrated hereinafter, the glass ceramic of the present invention has an astonished high mechanical strength without reduction of the chemical bonding strength with the bone in comparison with the known glass ceramic containing the $SiO_2$ of 41% or less.

When $P_2O_5$ content is less than 8%, a resultant glass composition has an increased devitrification so that the glass powder cannot be obtained. Further, an insufficient amount of apatite crystals can only be precipitated in the glass. Therefore, the content of $P_2O_5$ is 8% at minimum and preferably 8.2% or more. When the amount exceeds 25%, the precipitated wollastonite crystals decrease in amount. Therefore, $P_2O_5$ content is preferably 25% or less and 30% at maximum. Considering the mechanical strength of the resultant glass ceramic, it is recommended that $P_2O_5$ content is 10% or less.

$B_2O_3$, $F_2$, and $Al_2O_3$ are optional elements, and $B_2O_3$ and $F_2$ are used for stably precipitating the apatite crystals in the glass ceramic.

When the content of $B_2O_3$ exceeds 5%, it takes a long time period until the resultant glass ceramic forms a chemical bonding with the bone. Therefore, the content is limited up to 5% and preferably 4% or less.

When $F_2$ is used more than 5%, a resultant glass composition has a high crystallization rate and is degraded for sintering. Therefore, the content is 5% at maximum and preferably 3% or less.

In order to form the apatite crystals reliably, it is desired to use at least one of $B_2O_3$ and $F_2$ by 0.05% or more. However, when the total content exceeds 5%, a resultant glass is apt to phase-separate and has a difficulty for glass shaping.

When $Al_2O_3$ is more than 10%, a resultant glass ceramic has a reduced biological affinity and cannot make the chemical bonding with the bone.

In a method for producing the glass ceramic of the present invention, the heat treatment at a temperature within the glass powder sintering temperature range is important to obtain the glass ceramic which is substantially non-porous and has a high mechanical strength. While, the other heat treatment at a temperature within the crystallizing temperature range is important for precipitating a number of fine and dense crystals, that is, apatite, wollastonite, and diopside crystals in the glass.

The preparation of glass powder having particle size of 200 mesh or less is important to obtain the glass ceramic by the heat treatments which is substantially non-porous and has a crystal structure wherein the apatite, wollastonite, and diopside crystals are fine and uniformly dispersed and interlace to one another. If a glass body having a desired shape is formed directly from a molten glass without forming the glass powder and if the glass body is heat-treated for crystallization, the wollastonite and diopside crystals precipitate in only the surface of the glass body and cracks or cavities are formed in the body, so that the resultant glass ceramic is low in the mechanical strength.

The term of "glass powder sintering temperature range" means a temperature range from a thermal contraction starting temperature to a thermal contraction finishing temperature. The glass powder sintering temperature range is determined by observing the thermal contraction of the glass powder heated at a constant temperature elevating rate.

The term of "crystallizing temperature range" means a temperature range from a temperature at which exothermic crystal precipitation is started to a temperature at which the exothermic crystal precipitation is finished. The crystallizing temperature range is determined by performing the differential thermal analysis of the glass powder heated at a constant temperature elevating rate.

EXAMPLES

Table 1 demonstrates ingredients of various glass ceramics according to the present invention and their bending strength.

Each sample was produced as follows.

A glass batch comprising ingredients for each sample was prepared using oxides, carbonates, phosphates, fluorides and the like. The glass batch was inserted in a platinum crucible and was melted in an electric furnace at 1400°–1500° C. for 4 hours. Then, the molten glass was flowed between rolls cooled by water to form a glass ribbon. The ribbon was crushed down or milled to form a glass powder having particle size of 200 mesh or less. The powder was pressed to a compact body having a desired shape by use of a hydraulic press. The compact body was heated in an electric furnace from the room temperature to an elevated temperature of 1050° C. at a temperature elevating rate of 30°–60° C./hour and was kept at 1050° C. for 2–10 hours for sintering and crystallizing the body. Then, the body was cooled to the room temperature at a rate of 30°–120° C./hour, and a glass ceramic was obtained.

Each of the glass ceramic samples as thus produced had a number of apatite, wollastonite, and diopside crystals and a fine structure where those crystals interlace with one another and were dispersed in the glass phase.

The porosity of each sample is only 0.3% or less and, therefore, the glass ceramic samples are substantially non-porous.

Further, each sample has a mechanical strength (bending strength) of 2,000 Kg·f/cm$^2$ or more which is quite high in comparison with any known glass ceramics. The mechanical strength was measured as to a rod of 5×5×20 mm of each glass ceramic sample by the three-point loading test.

Those samples have excellent biological affinity and make sufficient chemical bonding with bone similar to the known biocompatible glass ceramics.

A bonding strength to the bone was measured with respect to 10×10×2 mm size plate specimens of No. 6 sample in Table 1, a polycrystalline alumina, a sintered apatite, and a glass ceramic disclosed in the above-described Japanese patent application No. 191252/'82. The measurement was carried out by inserting each plate specimen into a tibia condyle of a mature rabbit. After 8 weeks, the plate specimen was extracted together with bone surrounding the plate specimen and it was pulled apart from the bone. A force required to pull the plate specimen apart from the bone was appreciated as the bonding strength.

TABLE 1

| Ingredients | Samples | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| MgO (wt %) | 13 | 7.5 | 8 | 11 | 14 | 11.2 | 13.0 | 12.9 | 9.7 | 11.5 | 12.5 | 13 | 11.5 | 12.3 | 9.5 | 12.5 | 11.0 |
| CaO (wt %) | 36 | 37.5 | 32.5 | 25 | 30 | 35 | 33.4 | 25.5 | 28.5 | 30.0 | 33.5 | 31.4 | 27.0 | 25.1 | 25.0 | 34.3 | 35.0 |
| SiO$_2$ (wt %) | 41.5 | 41.5 | 44.5 | 41.5 | 43 | 43.5 | 44.0 | 47.0 | 47.3 | 47.5 | 44.0 | 43.2 | 44.0 | 46.5 | 41.5 | 44.0 | 43.0 |
| P$_2$O$_5$ (wt %) | 8.5 | 9.5 | 14.0 | 21.5 | 12.4 | 8.2 | 9.2 | 12.6 | 13.0 | 10.0 | 9.2 | 12.2 | 9.0 | 13.1 | 20.0 | 9.2 | 9.9 |
| B$_2$O$_3$ (wt %) | 1.0 | 4.0 | 1.0 | 1.0 | 0.6 | 0.1 | 0.4 | 2.0 | 1.0 | | | | | 2.0 | | | |
| F$_2$ (wt %) | | | | | | | | | | 1.0 | 0.8 | 0.2 | 2.5 | 1.0 | 1.5 | | 1.1 |
| Al$_2$O$_3$ (wt %) | | | | | | 2.0 | | | 0.5 | | | | 6.0 | | 2.5 | | |
| Bending Strength (kg · f/cm$^2$) | 2300 | 2200 | 2200 | 2250 | 2200 | 2300 | 2300 | 2100 | 2000 | 2200 | 2250 | 2250 | 2100 | 2200 | 2200 | 2300 | 2300 |

The measured bonding strength is shown in Table 2. It is noted from Table 2 that the specimen of No. 6 sample according to the present invention has a bonding strength which is equal to the specimen of the glass ceramic disclosed in Japanese patent application No. 191252/'82 but is higher than the polycrystalline alumina and the sintered apatite.

TABLE 2

| Specimens | Specimen by JPN PAT APPLN 191252/'82 | Specimen of No. 6 of this invention | Sintered apatite | Polycrystalline alumina |
|---|---|---|---|---|
| Amount of apatite in specimen | 35% | 15 | 100 | 0 |
| Ingredients | | | | |
| SiO$_2$ | 30.0 wt % | 44.0 | | |
| P$_2$O$_5$ | 16.2 | 9.2 | | |
| CaO | 47.7 | 34.3 | | |
| MgO | 6.1 | 12.5 | | |
| Bending Strength (kg) | 1400 | 2300 | 1100 | 4000 |
| Bonding Strength (kg · f/cm$^2$) | 9 | 9 | 6 | 0.2 |

Further, Table 2 teaches that the specimen according to the present invention has a high mechanical strength which is lower than the alumina specimen but is twice the other two specimens.

What is claimed is:

1. A high-strength biocompatible glass ceramic substantially free of alkali having a composition consisting essentially, by weight, of 7.2–16% MgO, 20–45% CaO, 41.5–50% SiO$_2$, 8–30% P$_2$O$_5$, 0–5% B$_2$O$_3$, 0–5% F$_2$, and 0–10% Al$_2$O$_3$, a total content of MgO, CaO, SiO$_2$, and P$_2$O$_5$ being 90% or more, said glass ceramic being substantially non-porous and having a mechanical strength of 2,000 Kg·f/cm$^2$ or more and a crystal structure where a number of fine crystals are densely dispersed in a glass phase, said fine crystals comprising apatite, wollastonite, and diopside crystals extending to interlace with one another in a complicated form.

2. A biocompatible glass ceramic as claimed in claim 1, having a composition which consists essentially, by weight, of 7.2–14% MgO, 25–38% CaO, 41.5–50% SiO$_2$, 8.2–25% P$_2$O$_5$, 0–4% B$_2$O$_3$, 0–3% F$_2$, and 0–6% Al$_2$O$_3$.

3. A biocompatible glass ceramic as claimed in claim 1, wherein a total content of B$_2$O$_3$ and F$_2$ is 0.05–5%.

* * * * *